(12) United States Patent
Lee et al.

(10) Patent No.: US 11,951,062 B2
(45) Date of Patent: Apr. 9, 2024

(54) DEVICE FOR VEHICLE FOR SUPPORTING AND MASSAGING PASSENGER'S NECK

(71) Applicants: Hyundai Motor Company, Seoul (KR); Kia Motors Corporation, Seoul (KR)

(72) Inventors: Baek Hee Lee, Suwon-Si (KR); Gyu Ho Chung, Yongin-Si (KR); Jong Hun Lee, Hwaseong-Si (KR); Yo Seob Lee, Incheon (KR); Hyun Kyu Park, Hwaseong-Si (KR); Min Hyuk Kwak, Suwon-Si (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 608 days.

(21) Appl. No.: 17/142,049

(22) Filed: Jan. 5, 2021

(65) Prior Publication Data
US 2022/0031559 A1 Feb. 3, 2022

(30) Foreign Application Priority Data

Jul. 29, 2020 (KR) ........................ 10-2020-0094155

(51) Int. Cl.
*A61H 15/00* (2006.01)
*B60K 35/00* (2006.01)
(Continued)

(52) U.S. Cl.
CPC ......... *A61H 15/00* (2013.01); *A61H 15/0078* (2013.01); *B60K 35/00* (2013.01);
(Continued)

(58) Field of Classification Search
CPC .... B60N 2/2872; B60N 2/2851; B60N 2/868; B60N 2/882; B60N 2/885; B60N 2002/022; B60N 2/976; B60N 2/002; B60N 2/0228; B60N 2/829; B60N 2/879; B60N 2/914; B60N 2/80; B60N 2/894; B60N 2002/899; A47C 7/383; A61H 15/00; A61H 15/0078; A61H 2015/0042; A61H 2201/0103; A61H 2201/1207; A61H 2201/1215; A61H 2201/123; A61H 2201/1607; A61H 2201/1611; A61H 2201/1671; A61H 2201/5046; A61H 2201/5092; A61H 2203/0431; A61H 2205/04;
(Continued)

(56) References Cited

U.S. PATENT DOCUMENTS

2001/0054837 A1* 12/2001 O'Connor ............ B60N 2/2872
297/397
2004/0217639 A1* 11/2004 Clough .................... A47C 7/38
297/391
(Continued)

*Primary Examiner* — Quang D Thanh
(74) *Attorney, Agent, or Firm* — MORGAN, LEWIS & BOCKIUS LLP (57) ABSTRACT

A device configured for a vehicle for supporting and massaging a neck of a passenger is provided. The device is configured such that a neck support pad is integrally formed on a lower end portion of a headrest to hold up and support the neck of a passenger, and a massage device is mounted in the neck support pad to massage the neck of the passenger, thus stably supporting and massaging the neck of the passenger sitting on a seat.

17 Claims, 9 Drawing Sheets

(51) Int. Cl.
    *B60N 2/90*    (2018.01)
    *B60R 11/04*    (2006.01)
    *A61B 5/18*    (2006.01)
    *B60K 35/10*    (2024.01)
    *B60R 11/00*    (2006.01)

(52) U.S. Cl.
CPC .............. *B60N 2/976* (2018.02); *B60R 11/04* (2013.01); *A61B 5/18* (2013.01); *A61H 2015/0042* (2013.01); *A61H 2201/0103* (2013.01); *A61H 2201/1207* (2013.01); *A61H 2201/1215* (2013.01); *A61H 2201/123* (2013.01); *A61H 2201/1607* (2013.01); *A61H 2201/1611* (2013.01); *A61H 2201/1671* (2013.01); *A61H 2201/5046* (2013.01); *A61H 2201/5092* (2013.01); *A61H 2203/0431* (2013.01); *A61H 2205/04* (2013.01); *A61H 2230/855* (2013.01); *B60K 35/10* (2024.01); *B60K 2360/115* (2024.01); *B60K 2360/1438* (2024.01); *B60R 2011/0003* (2013.01)

(58) Field of Classification Search
CPC ...... A61H 2230/855; A61H 2201/0149; A61H 2201/1604; A61H 2201/1609; A61H 2201/1664; A61H 2201/5025; A61H 2230/065; A61H 2230/825; A61H 23/006; A61H 23/02; B60K 35/00; B60K 35/10; B60K 2360/115; B60K 2360/1438; B60R 11/04; B60R 2011/0003; A61B 5/18; A61B 2503/22; A61B 5/024; A61B 5/0507; A61B 5/1116; A61B 5/1128; A61B 5/6893
See application file for complete search history.

(56) References Cited

U.S. PATENT DOCUMENTS

| | | | | |
|---|---|---|---|---|
| 2007/0246979 | A1* | 10/2007 | Browne | B60N 2/806 297/216.12 |
| 2015/0126916 | A1* | 5/2015 | Hall | A61H 9/0078 601/149 |
| 2020/0215949 | A1* | 7/2020 | Carles | B60N 2/806 |

* cited by examiner

DEVICE FOR VEHICLE FOR SUPPORTING AND MASSAGING PASSENGER'S NECK

CROSS REFERENCE TO RELATED APPLICATION

The present application claims priority to Korean Patent Application No. 10-2020-0094155, filed Jul. 29, 2020, the entire contents of which is incorporated herein for all purposes by this reference.

BACKGROUND OF THE INVENTION

Field of the Invention

The present invention relates to a device for a vehicle for supporting and massaging a neck of a passenger. More particularly, the present invention relates to a device for a vehicle for supporting and massaging a neck of a passenger, in which a neck support pad is integrally formed on a headrest, thus stably supporting and massaging a neck of a passenger sitting on a seat.

Description of Related Art

As is well known to people, a vehicle seat includes a seat cushion on which a lower body of a passenger sits, a seatback against which a passenger's back rests, and a headrest which supports the neck and the head.

A stay protrudes from a lower portion of the headrest. The present stay is inserted into the seatback to be movable upwards and downwards.

Thus, when the stay moves to a desired position, a height of the headrest may be adjusted.

However, a conventional headrest has the following problems.

First, the conventional headrest is problematic in that the head and the neck of a passenger having a small body size are not properly supported.

Figure 13:
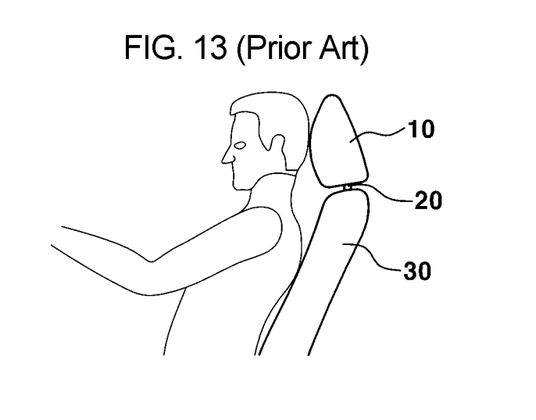
FIG. 13 is a schematic view showing an example where a head of a passenger is supported by a conventional headrest.

Referring to FIG. 13, even if a stay 20 is maximally inserted into a seatback 30 to adjust a headrest 10 to the lowest height, the head of a passenger who is small in body size and height is supported on a lower portion of the headrest 10, so that the neck of the passenger is folded, thus causing inconvenience.

Second, the conventional headrest is problematic in that the neck of a passenger is not properly supported.

In other words, even if the head of the passenger is supported by the headrest 10, the neck of the passenger is not supported by the headrest 10, thus causing the passenger to feel uncomfortable.

Figure 14:
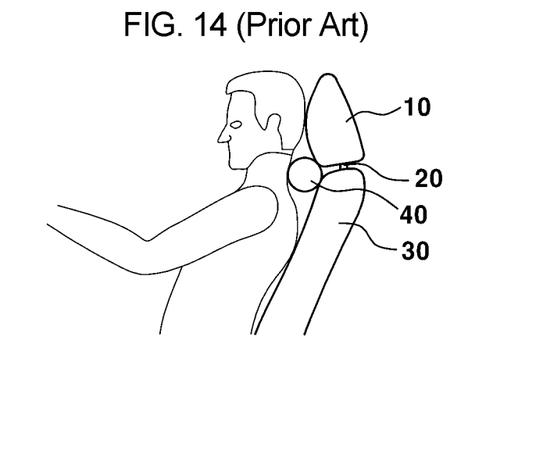
FIG. 14 is a schematic view showing a state where a separate neck support is mounted on the conventional headrest to be used.

Thus, as shown in FIG. 14, since a neck support 40 having a massage function is separately purchased and then mounted on the headrest 10, a separate purchase cost is undesirably required.

Therefore, there is a demand for a headrest that can comfortably support the head and neck of a passenger while adjusting the height of the headrest according to the passenger's body type, and has the function of reducing fatigue by massaging the neck.

The information included in this Background of the Invention section is only for enhancement of understanding of the general background of the invention and may not be taken as an acknowledgement or any form of suggestion that this information forms the prior art already known to a person skilled in the art.

BRIEF SUMMARY

Various aspects of the present invention are directed to providing a device for a vehicle for supporting and massaging a neck of a passenger, in which a neck support pad is integrally formed on a lower end portion of a headrest to hold up and support the neck of a passenger, and a massage device is mounted in the neck support pad to massage the neck of the passenger, thus stably supporting and massaging the neck of the passenger sitting on a seat.

To achieve the objective of the present invention, various aspects of the present invention provide a device for a vehicle for supporting and massaging a neck of a passenger, the device including a neck support pad integrally formed on a lower end portion of a headrest to support the neck of the passenger; a skeleton frame including a front frame that has guide holes on first and second sides of the front frame, a rear frame which is provided behind the front frame to be spaced from therefrom, and wing-out frames that are rotatably mounted on the first and second sides of the front frame, the skeleton frame mounted in the neck support pad; a plurality of main air cells mounted on a front of the front frame to be spaced from each other at a predetermined interval in a vertical direction of the vehicle and to be expanded or contracted, thus supporting a rear portion of the neck of the passenger; a side air cell mounted on a front of each of the wing-out frames to be expanded or contracted, thus supporting a side portion of the neck of the passenger; a lifting and driving device mounted on the rear frame to be driven when a massage mode is selected; and a massage ball connected to the lifting and driving device to selectively protrude forwards through each of the guide holes of the front frame, and lifted when the lifting and driving device is driven to massage the neck of the passenger.

The lifting and driving device may include a lift rail mounted on the rear frame; a lift bar inserted and fastened to the lift rail to be lifted along the lift rail; a first motor mounted on a rear surface of the lift rail; a friction roller mounted on an output shaft of the first motor; a wire connected at both end portions thereof to upper and lower portions of the lift bar while being in friction contact with the friction roller; and a support bracket mounted on first and second end portions of the lift bar to be connected to the massage ball.

The lifting and driving device may further include a solenoid mounted on the support bracket; and a plunger connected between the solenoid and the massage ball to transmit a linear moving force of the solenoid to the massage ball.

A guide roller may be attached to each of upper and lower end portions of the lift rail to guide circulation of the wire.

Hollow hinge end portions may be formed on both end portions of the front frame, and a hinge pin may be mounted on an internal end portion of each of the wing-out frames to be inserted into the hollow hinge end portions.

A second motor may be connected to the hinge pin to adjust an angle of each of the wing-out frames.

The device may further include a stay mounted on the rear frame to be inserted into and fastened to a seatback; a guide frame mounted on a lower portion of the stay; a third motor mounted on a rear surface of the rear frame; and a lead screw connected to an output shaft of the third motor, and fastened to the guide frame to be rotatable at the same place.

The device may further include an input portion through which a passenger selects whether to massage or not and selects a massage mode; a heart-rate measuring portion mounted at a predetermined position in the vehicle to monitor a heart rate of the passenger sitting on a seat; a body measuring portion mounted at a predetermined position in the vehicle to measure a body size of the passenger; and a controller configured of executing one of a plurality of massage modes depending on an input signal of the input portion, a monitoring signal of the heart-rate measuring portion, and a measurement signal of the body measuring portion.

To be more specific, the device configured for supporting and massaging the neck according to various exemplary embodiments of the present invention may further include a heart-rate sensing radar which is mounted in a vehicle to monitor a fatigue degree of a passenger sitting on a seat and then transmit the fatigue degree to a controller; a camera which is mounted at a predetermined position in the vehicle to monitor a position of the neck which is a body portion of the passenger to be massaged and then transmit the neck position to the controller; a touch screen that guides a menu to allow the passenger to select whether to massage or not and select a massage mode and simultaneously transmits a selected mode signal to the controller; and the controller that executes one of a plurality of massage modes according to a monitoring signal of the heart-rate detecting radar, an image signal of a camera, and a touch input signal of the touch screen.

Through the above-described means for solving problems occurring, various aspects of the present invention provide the following effects.

First, it is possible to comfortably support the neck as well as the head of a passenger by controlling the expansion and contraction of a main air cell.

Second, it is possible to reduce the fatigue of a passenger by massaging the neck of the passenger using a massage ball which is driven according to various drive modes.

Third, it is possible to prevent the head of a passenger from being tilted to one side by expanding a side air cell during sleeping, thus providing a stable resting posture for the passenger.

Fourth, it is possible to improve the marketability of a seat by obviating the necessity of separately purchasing an existing neck support.

The methods and apparatuses of the present invention have other features and advantages which will be apparent from or are set forth in more detail in the accompanying drawings, which are incorporated herein, and the following Detailed Description, which together serve to explain certain principles of the present invention.

It may be understood that the appended drawings are not necessarily to scale, presenting a somewhat simplified representation of various features illustrative of the basic principles of the present invention. The specific design features of the present invention as included herein, including, for example, specific dimensions, orientations, locations, and shapes will be determined in part by the particularly intended application and use environment.

In the figures, reference numbers refer to the same or equivalent portions of the present invention throughout the several figures of the drawing.

DETAILED DESCRIPTION

Reference will now be made in detail to various embodiments of the present invention(s), examples of which are illustrated in the accompanying drawings and described below. While the present invention(s) will be described in conjunction with exemplary embodiments of the present invention, it will be understood that the present description is not intended to limit the present invention(s) to those exemplary embodiments. On the other hand, the present invention(s) is/are intended to cover not only the exemplary embodiments of the present invention, but also various alternatives, modifications, equivalents and other embodiments, which may be included within the spirit and scope of the present invention as defined by the appended claims.

Hereinafter, exemplary embodiments of the present invention will be described in detail with reference to the accompanying drawings.

FIG. 1, FIG. 2, FIG. 3, FIG. 4, and FIG. 5 show a device configured for a vehicle for supporting and massaging a neck of a passenger according to various exemplary embodiments of the present invention.

Figure 5:
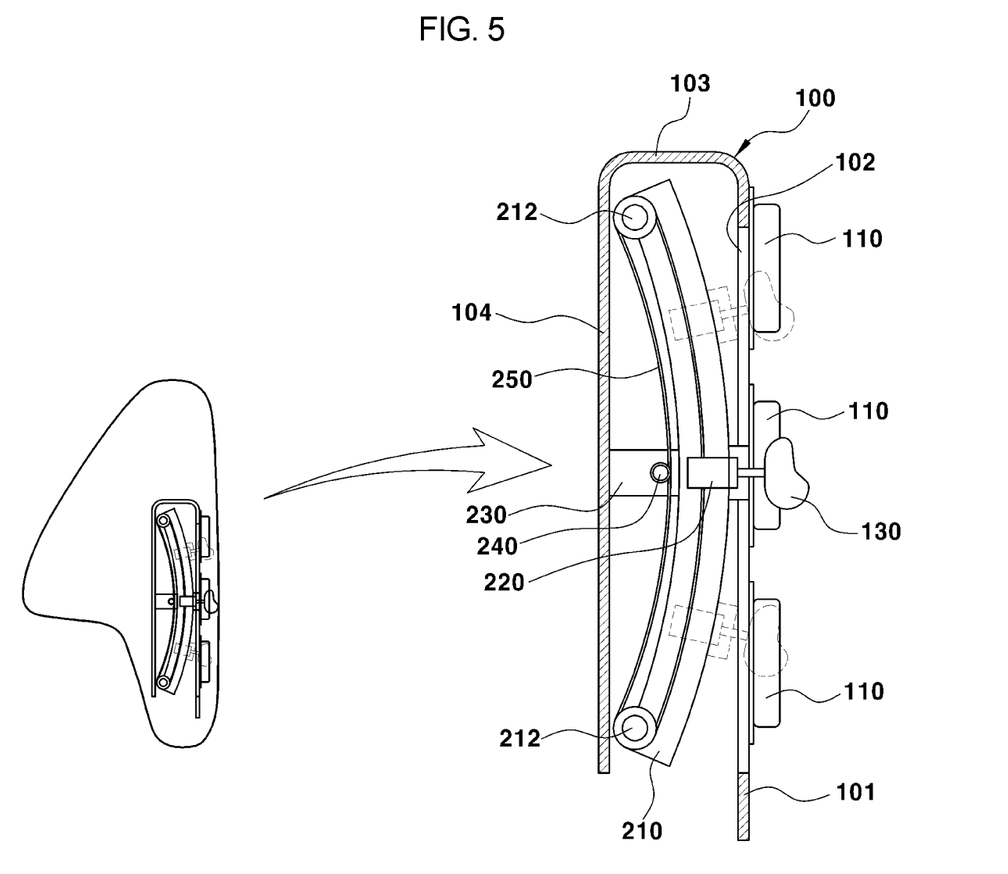
FIG. 5 is a plan sectional view showing the mounted state of the device configured for the vehicle for supporting and massaging the neck of the passenger according to various exemplary embodiments of the present invention.

Referring to FIG. 5, a neck support pad 20 for supporting the neck of the passenger is integrally formed on a lower end portion of a headrest 10.

Thus, while a passenger rests against the headrest 10, the neck of the passenger may be in close contact with and supported by the neck support pad 20.

Components and instruments are mounted in the neck support pad 20 to adjust a support pressure and a support position for the neck of the passenger and provide a massage function for the neck.

To the present end, a skeleton frame 100 is mounted in the neck support pad 20.

Figure 1:
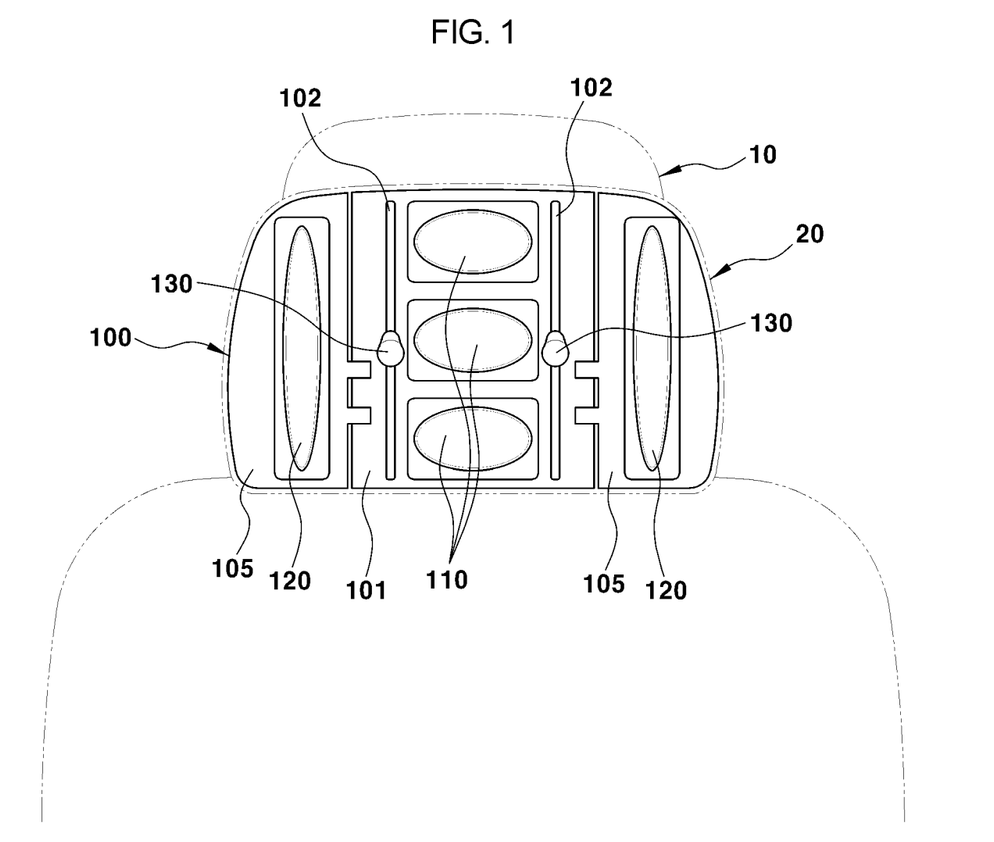
FIG. 1 is a front view showing a device configured for a vehicle for supporting and massaging a neck of a passenger according to various exemplary embodiments of the present invention.
Figure 2:
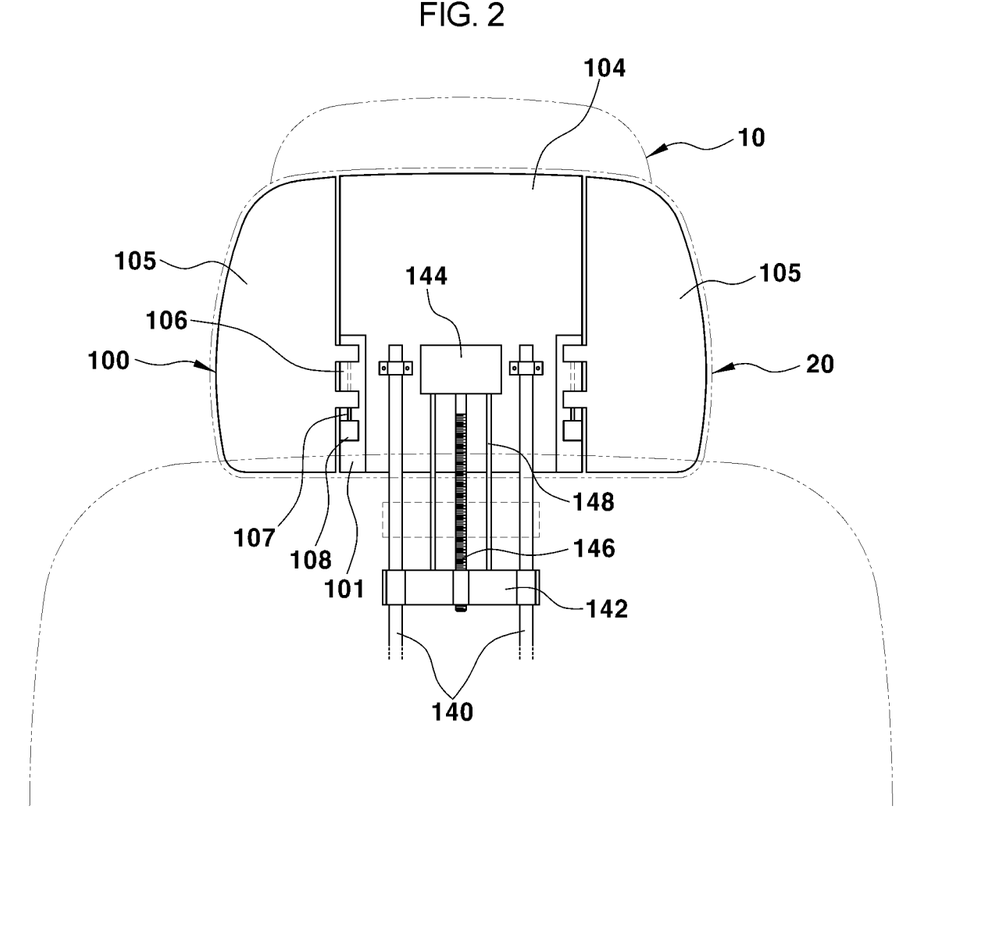
FIG. 2 is a rear view showing the device configured for the vehicle for supporting and massaging the neck of the passenger according to various exemplary embodiments of the present invention.
Figure 3:
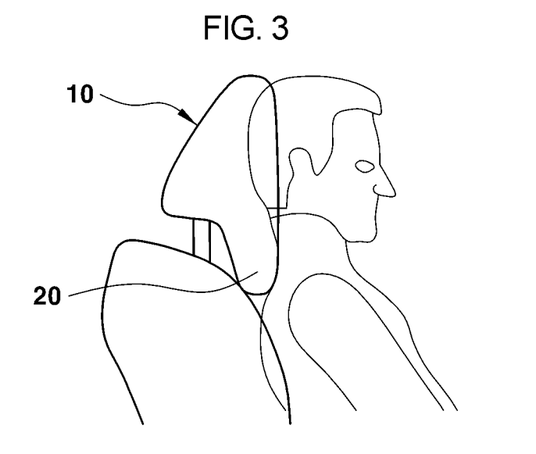
FIG. 3 is a side view showing an appearance of the device configured for the vehicle for supporting and massaging the neck of the passenger according to various exemplary embodiments of the present invention.

As shown in FIG. 1, FIG. 2, and FIG. 3, the skeleton frame 100 includes a front frame 101 having guide holes 102 on both sides thereof, a rear frame 104 provided behind the front frame 101 to be spaced from therefrom, and wing-out frames 105 rotatably mounted on both sides of the front frame 101.

The front frame 101 and the rear frame 104 are connected at upper end portions thereof to each other by a connecting frame 103 to be integrated with each other.

Among the components of the skeleton frame 100, a plurality of main air cells 110 is mounted on a front of the front frame 101 to be expanded or contracted, thus supporting a rear portion of the neck of the passenger.

Figure 4:
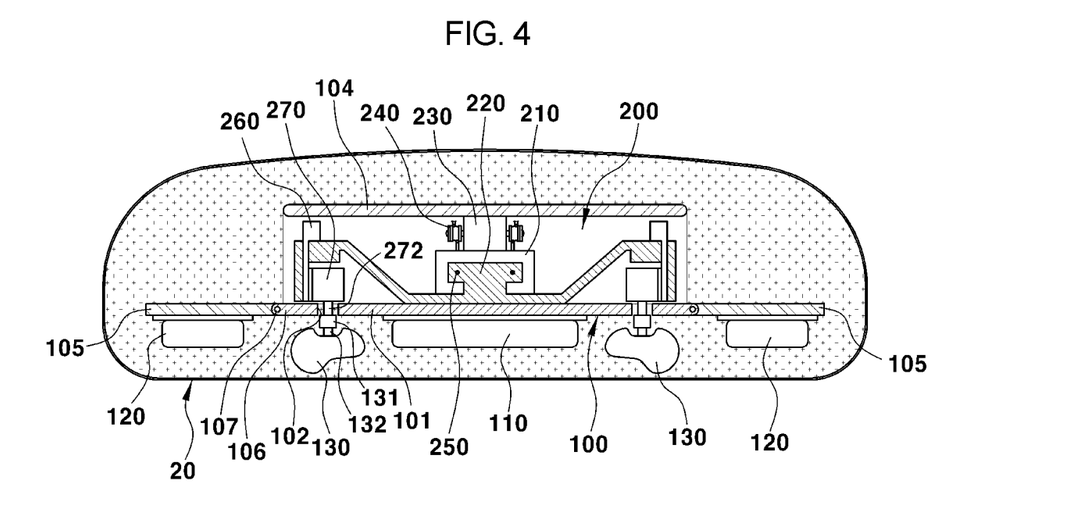
FIG. 4 is a side sectional view showing a mounted state of the device configured for the vehicle for supporting and massaging the neck of the passenger according to various exemplary embodiments of the present invention.

In detail, as shown in FIGS. 1 and 4, at least three or more main air cells 110 is mounted on the front of the front frame 101 to be spaced from each other at a predetermined interval in a vertical direction of the vehicle thereof, thus increasing or reducing the support pressure of a desired portion in a vertical region of the neck of the passenger.

Furthermore, side air cells 120 are mounted on fronts of the wing-out frames 105 to be expanded or contracted, thus supporting side portions of the neck of the passenger.

For example, the side air cells 120 are expanded when a passenger sleeps, thus stably supporting the side portions of the neck of the passenger, and thereby preventing the head and neck of the passenger from being tilted to one side thereof.

According to various exemplary embodiments of the present invention, a massage ball 130 for massaging the neck of the passenger and a lifting and driving device 200 for moving the massage ball 130 upwards and downwards and driving the massage ball 130 forwards and backwards are mounted on the skeleton frame 100.

The massage ball 130 protrudes forwards through the guide hole 102 of the front frame 101, so that the massage ball is configured to massage the neck of the passenger while being lifted and moved forwards and backwards by the lifting and driving device 200. The lifting and driving device 200 is mounted on the rear frame 104 to lift the massage ball 130 and move massage ball 130 forwards and backwards when the passenger selects a massage mode.

To the present end, as shown in FIG. 4 and FIG. 5, the lifting and driving device 200 includes a lift rail 210 which is mounted on the rear frame 104 to be vertically mounted, a lift bar 220 which is inserted and fastened to the lift rail 210 to be lifted, a first motor 230 which is mounted on a rear surface of the lift rail 210, a friction roller 240 which is rotatably mounted on an output shaft of the first motor 230, a wire 250 which is connected at both end portions thereof to upper and lower portions of the lift bar 220 while being in friction contact with the friction roller 240, and a support bracket 260 which is mounted on each of opposite end portions of the lift bar 220 to be connected to the massage ball 130.

Here, guide rollers 212 are attached to upper and lower end portions of the lift rail 210 to guide the circulation of the wire 250.

Thus, when the first motor 230 is driven, the friction roller 240 connected to the output shaft of the first motor 230 is rotated to provide the frictional force to the wire 254, so that the wire 250 is lifted. Sequentially, the lift bar 220 to which both end portions of the wire 250 are connected is lifted along the lift rail 210.

Simultaneously, since the massage balls 130 connected to both end portions of the lift bar 220 via the support brackets 260 protrude forwards through the guide holes 102 of the front frame 101, the massage balls 130 are also lifted when the lift bar 220 is lifted, thus massaging the neck of the passenger.

In the instant case, a function of massaging the neck of the passenger while the massage ball 130 is lifted may be combined with a massage function of hitting the neck of the passenger while the massage ball 130 moves forwards and backwards to obtain better massage effects.

To the present end, a solenoid 270 is mounted on the support bracket 260, and a plunger 272 which is a forward and backward movement shaft of the solenoid 270 is connected to the massage ball 130.

Thus, when the plunger 272 is repeatedly moved forwards by current which is periodically applied to the solenoid 270 and the plunger 272 is repeatedly moved backwards to an original position of thereof by the periodic release of current, the massage ball 130 connected to the plunger 272 may perform a massage operation of hitting the neck of the passenger while moving forwards and backwards thereof.

As shown in FIG. 4, to allow the massage ball 130 to massage the neck of the passenger while performing both the forward and backward movement and the rotation, a fourth motor 131 may be mounted on a front end portion of the plunger 272 and a rotation shaft 132 of the fourth motor 131 may be connected to the massage ball 130.

Meanwhile, since the length and thickness of the neck of the passenger vary according to a body type, the angle of the wing-out frame 105 is preferably adjusted to be close to or distant from the side portion of the neck according to the body type of the passenger, thus allowing the side air cell 120 attached to the front of the wing-out frame 105 to stably the side portion of the neck of the passenger.

To the present end, as shown in FIG. 2, hollow hinge end portions 106 are formed on both end portions of the front frame 101, and a hinge pin 107 is fixedly mounted on an internal end portion of each wing-out frame 105 to be inserted into the hinge end portion 106, and an output shaft of a second motor 108 is connected to the hinge pin 107.

Thus, when a rotating force caused by the driving of the second motor 108 is transmitted to the hinge pin 107, the wing-out frame 105 is also rotated by the rotation of the hinge pin 107, so that the angle of the wing-out frame 105 may be adjusted to be close to or distant from the side portion of the neck according to the body type of the passenger.

Meanwhile, according to the body type of the passenger, it is preferable to automatically adjust the neck support height of the neck support pad 20.

To the present end, as shown in FIG. 2, a guide frame 142 is mounted on the stay 140 which is mounted on the rear frame 104 to be inserted into and fastened to the seatback, a third motor 144 is mounted on the rear surface of the rear frame 104, and a lead screw 146 fastened to the guide frame 142 to be rotatable at the same place is connected to an output shaft of the third motor 144.

Here, a guide bar 148 is attached to a housing of the third motor to be ejectably inserted into the guide frame 104.

Thus, when a rotating force caused by the driving of the third motor 144 is applied to the lead screw 146, the lead screw 146 is rotated at the same place, and simultaneously the guide frame 142 is lifted along the lead screw 146 and the guide bar 148. Furthermore, the stay 140 to which the guide frame 142 is mounted is lifted, and simultaneously the rear frame 104 to which the stay 140 is mounted is lifted. When the rear frame 104 is lifted, the skeleton frame 100 is lifted, so that the neck support height of the neck support pad 20 may be adjusted.

Here, the configuration and operation for controlling the driving of the neck supporting and massaging device according to various exemplary embodiments of the present invention are as follows.

Figure 6:
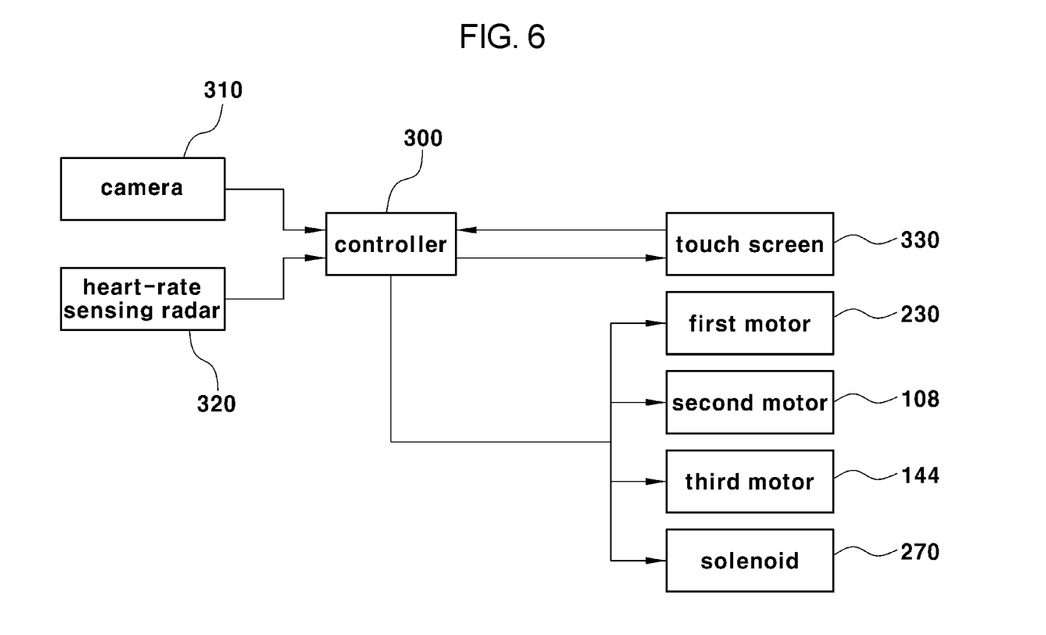
FIG. 6 is a diagram showing the configuration of a control system for driving the device configured for the vehicle for supporting and massaging the neck of the passenger according to various exemplary embodiments of the present invention.

Referring to FIG. 6, the configuration for controlling the driving of the device configured for the vehicle for supporting and massaging the neck of the passenger according to various exemplary embodiments of the present invention includes an input portion through which a passenger selects whether to massage or not and selects a massage mode; a heart-rate measuring portion mounted at a predetermined position in a vehicle to monitor a heart rate of a passenger sitting on a seat; a body measuring portion mounted at a predetermined position in the vehicle to measure a body size of the passenger; and a controller configured of executing one of a plurality of massage modes depending on an input signal of the input portion, a monitoring signal of the heart-rate measuring portion, and a measurement signal of the body measuring portion.

In detail, the configuration for controlling the driving of the device configured for the vehicle for supporting and massaging the neck of the passenger according to various exemplary embodiments of the present invention includes a camera 310 which is mounted at a predetermined position in the vehicle to photograph a head region including the surface and neck of the passenger and the neck support pad 20 and then transmit the photographed image to the controller 300, a heart-rate sensing radar 320 which is mounted at a predetermined position in the vehicle to monitor a heart-rate condition for determining the fatigue degree of the passenger sitting on the seat and then transmit the monitored result to the controller 300, a touch screen 330 that displays a menu through which the passenger selects whether to massage or not and selects the massage mode and simultaneously transmits a signal of the selected massage mode to the controller 300, and the controller 300 that executes a massage mode depending on the image signal of the camera 310, the monitoring signal of the heart-rate sensing radar 320, and the touch input signal of the touch screen 330.

The controller 300 receives the image signal of the camera 310 to compare a height of the head region of the passenger and a height of the neck support pad 20. When a height difference between the height of the head region of the passenger and the height of the neck support pad 20 is equal to or greater than a reference value, a current signal for lifting the neck support pad 20 is applied to the third motor 144.

Thus, when the rotating force caused by the driving of the third motor 144 is applied to the lead screw 146 in a response to the current signal of the controller 300, the rear frame 104 lifts the skeleton frame 100, and consequently the neck support height of the neck support pad 20 may be adjusted to fit for the head region of the passenger.

Figure 8:
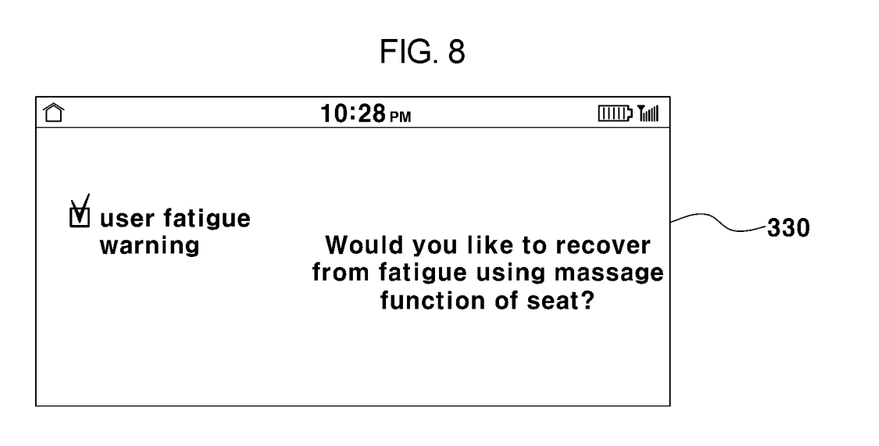
FIG. 8 is a schematic view showing a drive recommending operation of the device configured for the vehicle for supporting and massaging the neck of the passenger according to various exemplary embodiments of the present invention.

Furthermore, the controller 300 receives the monitoring signal of the heart-rate sensing radar 320 to compare a heart rate of the passenger and a normal heart rate. when a difference between the heart rate of the passenger and the normal heart rate is equal to or greater than a reference value, it is determined that the fatigue degree of the passenger is increased due to long driving or the like, so that a massage recommending message for reducing the fatigue is displayed on the touch screen 330, as shown in FIG. 8.

Thus, the passenger may read the message displayed on the touch screen 330, and then may execute the massage function.

Figure 7:
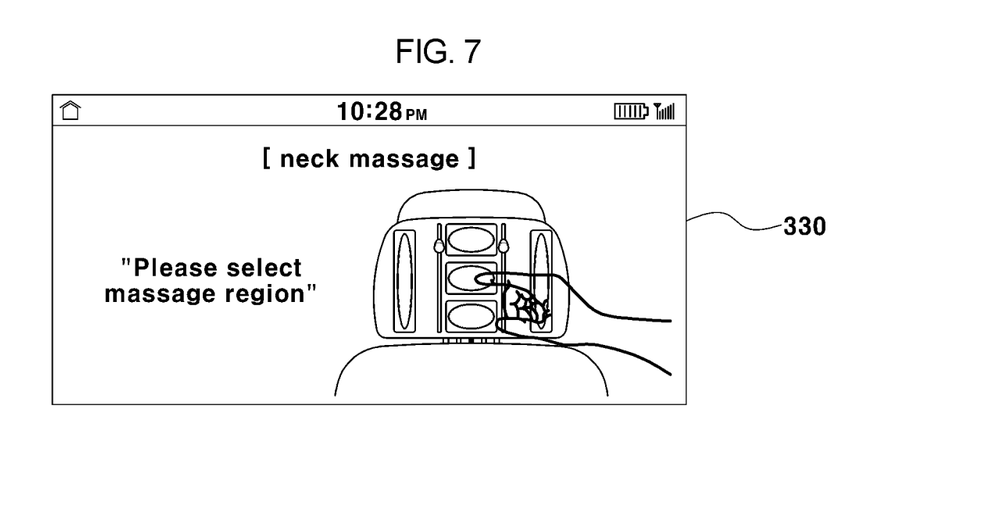
FIG. 7 is a schematic view showing a drive selecting operation of the device configured for the vehicle for supporting and massaging the neck of the passenger according to various exemplary embodiments of the present invention.

Furthermore, as shown in FIG. 7, the controller 300 receives the input signal selected by the passenger himself or herself touching the menu displayed on the touch screen 330 and then applies the current signal to the first motor 230 and the solenoid 270 to execute the selected massage mode in a response to the selected input signal.

Here, the driving example of the neck supporting and massaging device according to various exemplary embodiments of the present invention is as follows.

Figure 9:
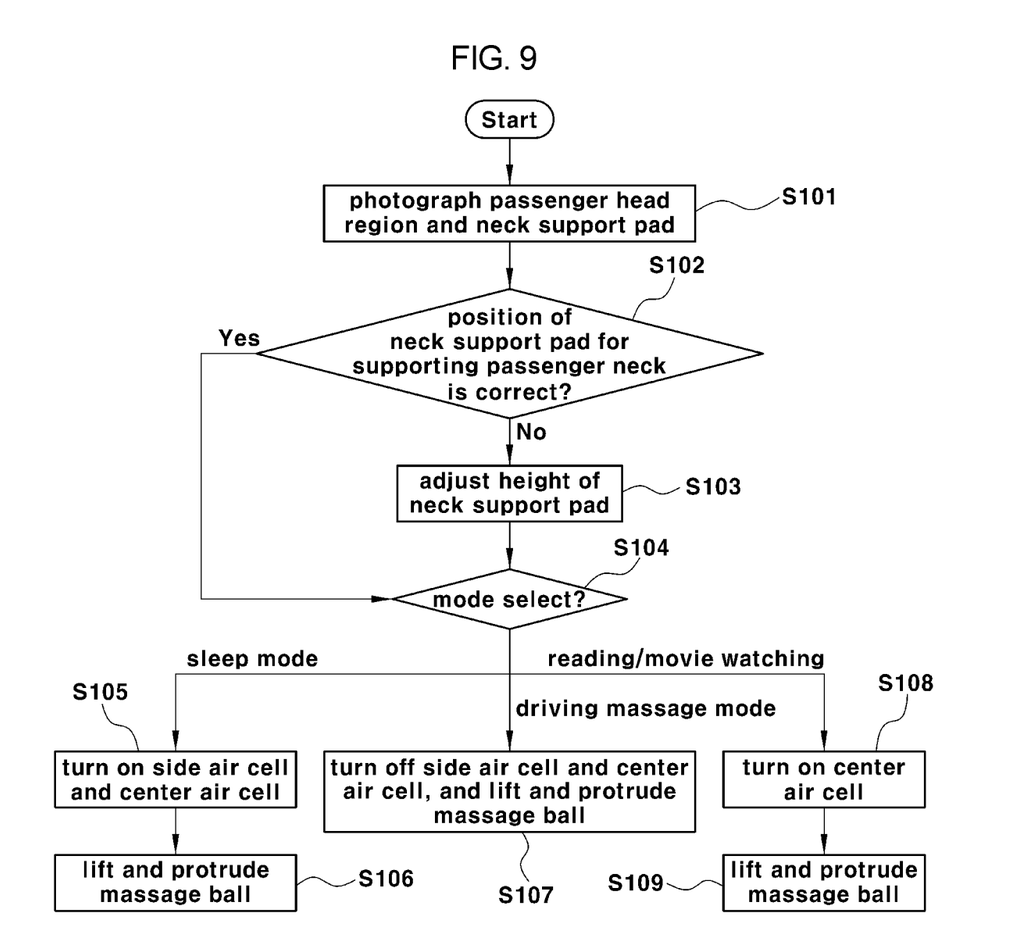
FIG. 9 is a flowchart showing a drive scenario of the device configured for the vehicle for supporting and massaging the neck of the passenger according to various exemplary embodiments of the present invention.

FIG. 9 is a flowchart showing a drive scenario of the device configured for the vehicle for supporting and massaging the neck of the passenger according to various exemplary embodiments of the present invention.

First, when the passenger sits on the seat, the camera 310 photographs the head region including the face and neck of the passenger and the neck support pad 20 (S101).

Subsequently, the image signal photographed by the camera 310 is transmitted to the controller 300, so that it is determined whether the height of the neck support pad 20 for supporting the neck of the passenger is correct (S102).

In other words, when the controller 300 receives the image signal of the camera 310, the height of the head region of the passenger and the height of the neck support pad 20 are compared with each other. When the height difference is equal to or greater than a reference height, the current signal for lifting the neck support pad 20 is applied to the third motor 144.

Thus, when the rotating force caused by the driving of the third motor 144 is applied to the lead screw 146, the rear frame 104 lifts the skeleton frame 100, so that the neck support height of the neck support pad 20 may be adjusted to fit for the head region of the passenger.

Therefore, the neck of the passenger is stably supported by the neck support pad 20, thus solving a problem of the related art, wherein a neck of a passenger is not supported by the headrest to cause inconvenience, and thereby allowing the neck to feel comfortable.

Next, the passenger may select various modes for driving the air cell and/or the massage ball.

For example, the controller 300 compares the heart rate of the passenger and the normal heart rate. When the difference is equal to or greater than the reference value, it is determined that the fatigue degree of the passenger is increased due to long driving or the like, so that the massage recommending message for reducing the fatigue is displayed on the touch screen 330, as shown in FIG. 8, and then the passenger may select the massage mode through the touch screen 330.

Alternatively, the passenger himself or herself may select the massage mode by touching the menu displayed on the touch screen 330.

Thus, when the controller 300 selects the massage mode, the current signal is applied to the first motor 230 and the solenoid 270.

Therefore, when the friction roller 240 caused by the driving of the first motor 230 is rotated, the frictional force is transmitted to the wire 250, so that the wire 250 is lifted.

Sequentially, the lift bar 220 to which both end portions of the wire 250 are connected is lifted along the lift rail 210, and simultaneously the massage balls 130 connected to both end portions of the lift bar 220 via the support brackets 260 are also lifted, thus massaging the neck of the passenger (S107).

Furthermore, the plunger 272 and the massage ball 130 move forwards and backwards by the driving of the solenoid 270, thus performing the massage operation of hitting the neck of the passenger (S107).

Simultaneously, the massage ball 130 is rotated by the driving of the fourth motor 131, thus massaging the neck of the passenger.

In contrast, when the passenger selects a sleep mode through the touch screen 330, the controller 300 transmits a driving signal to an air pump, so that the main air cells 110 and the side air cells 120 are expanded together (S105). In an exemplary embodiment of the present invention, the main air cells 110 and the side air cells 120 are connected to the same air pump with air distribution device connected to the controller to provide air to either or both of the main air cells 110 and the side air cells 120. In another exemplary embodiment of the present invention, the main air cells 110 and the side air cells 120 are connected to individual air pump with each air distribution device connected to the controller to provide air to the main air cells 110 and the side air cells 120, respectively.

Thus, the rear portion of the neck of the passenger may be stably supported by the expansion of the main air cells 110, and the side air cells 110 may stably support the side portions of the neck of the passenger, thus preventing the head and neck of the passenger from being tilted to one side, and thereby keeping the sleeping posture of the passenger comfortable.

In the instant case, when the passenger selects the sleep mode and then further selects the massage mode, the massage may be further performed by the lifting and the forward and backward movement of the massage ball 130 (S106).

Furthermore, when the passenger selects a reading and movie watching mode through the touch screen 330, the controller 300 transmits a driving signal to the air pump, so that each main air cell 110 is expanded (S108).

Thus, since the rear portion of the neck of the passenger is supported by the expansion of the main air cell 110 and simultaneously the neck of the passenger naturally is bowed to a book or a smart device, the passenger's posture may be changed into a posture for comfortably reading a book or watching a movie.

In the instant case, when the passenger selects the reading and movie watching mode and then further selects the massage mode, the massage may be further performed by the lifting and the forward and backward movement of the massage ball 130 (S109).

Meanwhile, the passenger may select one of several massage modes that are displayed through the touch screen 330, so that the passenger may select a desired massage intensity.

Figure 10:
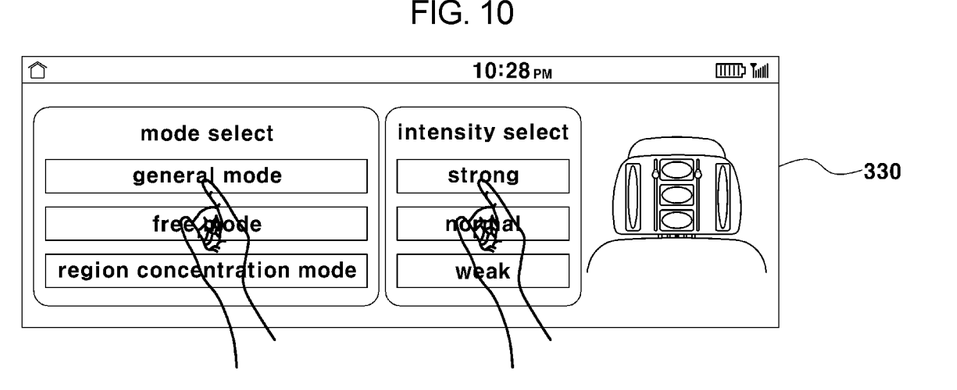
FIG. 10, FIG. 11, and FIG. 12 are schematic views showing a drive method of the device configured for the vehicle for supporting and massaging the neck of the passenger according to various exemplary embodiments of the present invention.

For example, as shown in FIG. 10, the passenger may select, as the massage mode, both a general mode (e.g., a mode in which the massage ball is lifted and moved forwards and backwards at a predetermined speed) and a strong massage mode (e.g., a mode in which the massage ball is moved forwards and backwards to a maximum distance).

Figure 11:
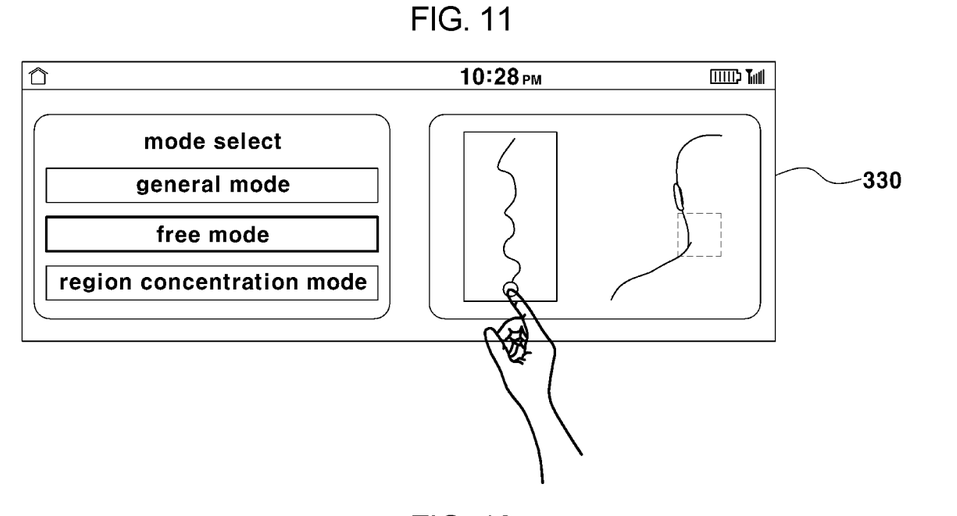

Furthermore, when the passenger selects a free mode as the massage mode as shown in FIG. 11, the passenger may drag on the touch screen to adjust the massage intensity which is to be generated by the lifting and the forward and backward movement of the massage ball.

Figure 12:
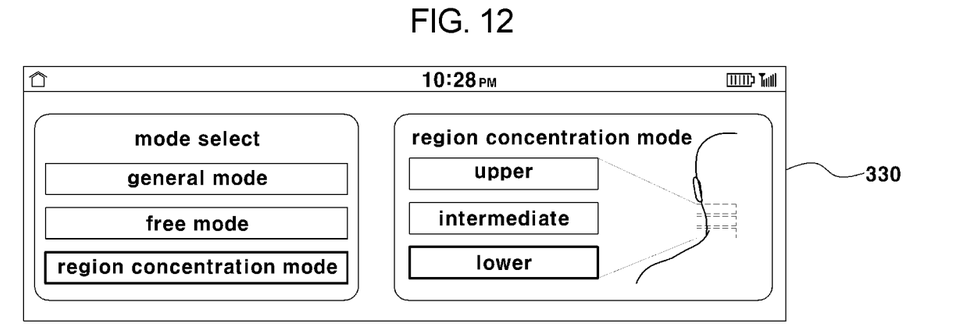

Furthermore, when the passenger selects a region concentration mode as the massage mode as shown in FIG. 12, the massage ball is stopped at one of upper/intermediate/lower positions during the lifting, and simultaneously, hitting caused by the forward and backward movement of the massage ball intensively massages a desired region.

As described above, the present invention controls the expansion and contraction of a main air cell to comfortably support the neck of a passenger, prevents the head of the passenger from being tilted to one side during sleeping by expanding a side air cell, thus providing a stable resting posture for the passenger, and reduces the fatigue of a passenger by massaging the neck of the passenger using a massage ball which is driven according to various drive modes.

Furthermore, the term "controller", "control unit" or "control device" refers to a hardware device including a memory and a processor configured to execute one or more steps interpreted as an algorithm structure. The memory stores algorithm steps, and the processor executes the algorithm steps to perform one or more processes of a method in accordance with various exemplary embodiments of the present invention. The controller according to exemplary embodiments of the present invention may be implemented through a nonvolatile memory configured to store algorithms for controlling operation of various components of a vehicle or data about software commands for executing the algorithms, and a processor configured to perform operation to be described above using the data stored in the memory. The memory and the processor may be individual chips. Alternatively, the memory and the processor may be integrated in a single chip. The processor may be implemented as one or more processors.

The controller or the control unit may be at least one microprocessor operated by a predetermined program which may include a series of commands for carrying out a method in accordance with various exemplary embodiments of the present invention.

The aforementioned invention can also be embodied as computer readable codes on a computer readable recording medium. The computer readable recording medium is any data storage device that can store data which may be thereafter read by a computer system. Examples of the computer readable recording medium include hard disk drive (HDD), solid state disk (SSD), silicon disk drive (SDD), read-only memory (ROM), random-access memory (RAM), CD-ROMs, magnetic tapes, floppy discs, optical data storage devices, etc and implementation as carrier waves (e.g., transmission over the Internet).

In various exemplary embodiments of the present invention, each operation described above may be performed by a controller, and the controller may be configured by a plurality of controllers, or an integrated single controller.

For convenience in explanation and accurate definition in the appended claims, the terms "upper", "lower", "inner", "outer", "up", "down", "upwards", "downwards", "front", "rear", "back", "inside", "outside", "inwardly", "outwardly", "interior", "exterior", "internal", "external", "inner", "outer", "forwards", and "backwards" are used to describe features of the exemplary embodiments with reference to the positions of such features as displayed in the figures. It will be further understood that the term "connect" or its derivatives refer both to direct and indirect connection.

Furthermore, the term of "fixedly connected" signifies that fixedly connected members always rotate at a same speed. Furthermore, the term of "selectively connectable" signifies "selectively connectable members rotate separately when the selectively connectable members are not engaged to each other, rotate at a same speed when the selectively connectable members are engaged to each other, and are stationary when at least one of the selectively connectable members is a stationary member and remaining selectively connectable members are engaged to the stationary member".

The foregoing descriptions of specific exemplary embodiments of the present invention have been presented for purposes of illustration and description. They are not intended to be exhaustive or to limit the present invention to the precise forms disclosed, and obviously many modifications and variations are possible in light of the above teachings. The exemplary embodiments were chosen and described to explain certain principles of the present invention and their practical application, to enable others skilled in the art to make and utilize various exemplary embodiments of the present invention, as well as various alternatives and modifications thereof. It is intended that the scope of the present invention be defined by the Claims appended hereto and their equivalents.

What is claimed is:

1. A device for supporting and massaging a neck of a passenger, the device comprising:
   a neck support pad integrally formed on a lower end portion of a headrest to support the neck of the passenger;
   a skeleton frame including a front frame that has guide holes on first and second sides of the front frame, a rear frame which is mounted behind the front frame to be spaced from the front frame, and wing-out frames that are rotatably mounted on the first and second sides of the front frame, the skeleton frame mounted in the neck support pad;
   at least a main air cell mounted on a front of the front frame to be expanded or contracted, for supporting a rear portion of the neck of the passenger;
   at least a side air cell mounted on a front of each of the wing-out frames to be expanded or contracted, for supporting a side portion of the neck of the passenger;
   a lifting and driving device mounted on the rear frame to be driven when a massage mode is selected; and
   a massage ball connected to the lifting and driving device to selectively protrude forwards through each of the guide holes of the front frame, and lifted when the lifting and driving device is driven to massage the neck of the passenger.

2. The device of claim 1, wherein the lifting and driving device includes:
   a lift rail mounted on the rear frame;
   a lift bar inserted and fastened to the lift rail to be lifted along the lift rail;
   a first motor mounted on a rear surface of the lift rail;
   a friction roller mounted on an output shaft of the first motor;
   a wire connected at first and second end portions thereof to upper and lower portions of the lift bar, respectively, while being in friction contact with the friction roller; and
   a support bracket mounted on first and second end portions of the lift bar to be connected to the massage ball.

3. The device of claim 2, wherein the lifting and driving device further includes:
   a solenoid mounted on the support bracket; and
   a plunger connected between the solenoid and the massage ball to transmit a linear moving force of the solenoid to the massage ball in a response to the selected massage mode.

4. The device of claim 2, wherein a guide roller is attached to each of the upper and lower end portions of the lift rail to guide circulation of the wire.

5. The device of claim 3, wherein a second motor is mounted on a front end portion of the plunger to selectively rotate the massage ball, and a rotation shaft of the second motor is connected to the massage ball.

6. The device of claim 1, wherein hollow hinge end portions are formed on first and second end portions of the front frame, and a hinge pin is mounted on an internal end portion of each of the wing-out frames to be inserted into the hollow hinge end portions.

7. The device of claim 6, wherein a motor is connected to the hinge pin to adjust an angle of each of the wing-out frames.

8. The device of claim 1, further including:
   a stay mounted on the rear frame to be inserted into and fastened to a seatback;
   a guide frame mounted on a lower portion of the stay;
   a motor mounted on a rear surface of the rear frame; and
   a lead screw connected to an output shaft of the motor, and fastened to the guide frame to be rotatable at a same place.

9. A system for supporting and massaging a neck of a passenger, the system comprising:
   a neck support pad integrally formed on a lower end portion of a headrest to support the neck of the passenger;
   a skeleton frame including a front frame that has guide holes on first and second sides of the front frame, a rear frame which is mounted behind the front frame to be spaced from the front frame, and wing-out frames that are rotatably mounted on the first and second sides of the front frame, the skeleton frame mounted in the neck support pad;
   at least a main air cell mounted on a front of the front frame to be expanded or contracted, for supporting a rear portion of the neck of the passenger;
   at least a side air cell mounted on a front of each of the wing-out frames to be expanded or contracted, thus supporting a side portion of the neck of the passenger;
   a lifting and driving device mounted on the rear frame to be driven when a massage mode is selected;
   a massage ball connected to the lifting and driving device to selectively protrude forwards through each of the guide holes of the front frame, and lifted when the lifting and driving device is driven to massage the neck of the passenger;
   an input portion through which the passenger selects whether to massage or not and selects the massage mode;
   a heart-rate measuring portion mounted at a predetermined position in a vehicle to monitor a heart rate of the passenger sitting on a seat;
   a body measuring portion mounted at a predetermined position in the vehicle to measure a body size of the passenger; and
   a controller configured of executing one of a plurality of modes depending on an input signal of the input portion, a monitoring signal of the heart-rate measuring portion, and a measurement signal of the body measuring portion, wherein the plurality of modes include the massage mode.

10. The system of claim 9, wherein the input portion includes a touch screen which is connected to the controller and mounted at a predetermined position in the vehicle to display a menu through which the passenger selects whether to massage or not and selects one of the plurality of modes and to transmit a signal of the selected mode to the controller.

11. The system of claim 10, wherein the controller is configured to receive the input signal selected by the passenger itself touching the menu displayed on the touch screen, and then to apply a current signal to the lifting and driving device connected to the controller to execute the selected massage mode in a response to the selected input signal.

12. The system of claim 9, wherein the plurality of modes includes:
   the massage mode, in which the controller performs massaging of the neck of the passenger via the lifting and driving device and the massage ball;
   a sleep mode, in which the controller is configured to expand the at least a main air cell and the at least a side air cell; and
   a reading and movie watching mode, in which the controller is configured to turn on the at least a main air cell.

13. The system of claim 10, wherein the heart-rate measuring portion includes a heart-rate sensing radar which is mounted at a predetermined position in the vehicle to monitor a fatigue degree of the passenger sitting on the seat and then to output a monitoring signal of the fatigue degree to the controller.

14. The system of claim 13, wherein the controller is configured to receive the monitoring signal of the heart-rate detecting radar, to compare a heart rate of the passenger and a normal heart rate, and then to display a massage recommending message for reducing fatigue of the passenger on the touch screen, when a difference between the heart rate of the passenger and the normal heart rate is equal to or greater than a reference value.

15. The system of claim 9, wherein the body measuring portion includes a camera which is mounted at a predetermined position in the vehicle to monitor a position of the neck of the passenger which is to be massaged and then to output a monitored position to the controller.

16. The system of claim 15, wherein the controller is configured to receive an image signal of the camera, to compare a height of a head region of the passenger and a height of the neck support pad, and then to apply a current signal to the lifting and driving device to lift the neck support pad when a height difference between the height of the head region of the passenger and the height of the neck support pad is equal to or greater than a reference value.

17. The system of claim 9, wherein the at least a main air cell is formed in plural and mounted on the front of the front frame to be spaced from each other at a predetermined interval in a vertical direction of the vehicle and to be expanded or contracted.

* * * * *